US006827684B2

United States Patent
Maruyama

(10) Patent No.: US 6,827,684 B2
(45) Date of Patent: Dec. 7, 2004

(54) MEDICAL DIAGNOSTIC APPARATUS WITH A FUNCTION FOR PREVENTING OVERSIGHT OMISSIONS OF DATA COLLECTION ITEMS

(75) Inventor: Toshie Maruyama, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 150 days.

(21) Appl. No.: 10/107,354

(22) Filed: Mar. 28, 2002

(65) Prior Publication Data

US 2002/0143254 A1 Oct. 3, 2002

(30) Foreign Application Priority Data

Mar. 29, 2001 (JP) .................................. P2001-096671

(51) Int. Cl.⁷ .............................................. A61B 8/00
(52) U.S. Cl. ....................................................... 600/437
(58) Field of Search ................................ 600/437, 443, 600/440, 441–447, 453–458, 407; 128/916

(56) References Cited

U.S. PATENT DOCUMENTS 5,553,620 A * 9/1996 Snider et al. ............... 600/440
5,919,138 A * 7/1999 Ustuner ...................... 600/443
6,001,061 A * 12/1999 Ogishima et al. ........... 600/440
6,149,594 A * 11/2000 Rock et al. .................. 600/437
6,454,712 B1 * 9/2002 Oonuki ....................... 600/437

* cited by examiner

Primary Examiner—Ali Imam
(74) Attorney, Agent, or Firm—Oblon, Spivak, McClelland, Maier & Neustadt, P.C.

(57) ABSTRACT

A medical diagnostic apparatus, such as an ultrasonic diagnostic apparatus, capable of performing various measurements or scans of a subject, including a measuring unit configured to measure data of the subject based on a scanned image, a monitor which displays the data and the image, an input device configured to input information of the subject and an interface such as a touch command screen (TCS) for selecting measurement items. When an operator selects a switch for a desired measurement item displayed on the TCS in a first form, the measuring unit measures the selected item. When the measurement is finished, the switch is displayed in a second form different from the first form.

33 Claims, 16 Drawing Sheets

| CARDIAC FUNCTION EXAM. | SWITCHES FOR MENU |
| --- | --- |
| PULMO VEIN | [S1] [S2] [D] [PVA] [ARDUR] [S-VTI] D-VTI] |
| PULMO VALVE | [PA TRACE] [P-VEL] [PA DIAM] [HR] [ET] [AT] [PEP] |
| TRICUSPID | [TR TRACE] [TV TRACE] [P-VEL] |
| AORTIC | [PWVEL] [CWVEL] [CW VTI] [PW TRACE] [LVOT DIAM] [PHT DCT] |
| MITRAL | [E] [A] [PHT DCT] [dP/dt] [E-DURATION] [A-DURATION] [IRT] [MV TRACE] [MV DIAM] [HR] |
FIG. 4
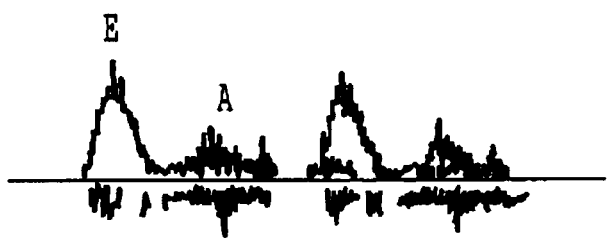
FIG. 5A
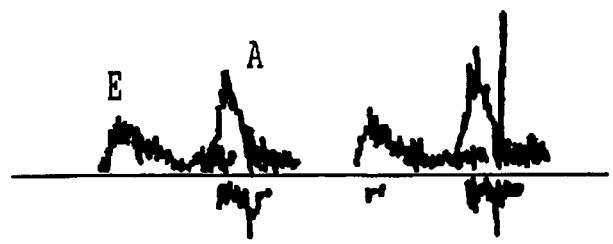
FIG. 5B

|  | | | | | PULMO VEIN | MIVA | RATIO |
|---|---|---|---|---|---|---|---|
| FLOW VOLUME | MV TRACE | MV DIAM | HR | | PULMO VALVE | PI | PG |
| DURATION | E-DUR ATION | A-DUR ATION | IRT | | TRICU SPID | FLOW VTI | VA VTI |
| VALVE AREA | PHT DCT | | dP/dt | | AOR TIC | VEL HISTO | TIME |
| E/A | E | A | | | MIT RAL | AUTO TRACE | VEL |

*FIG. 6*

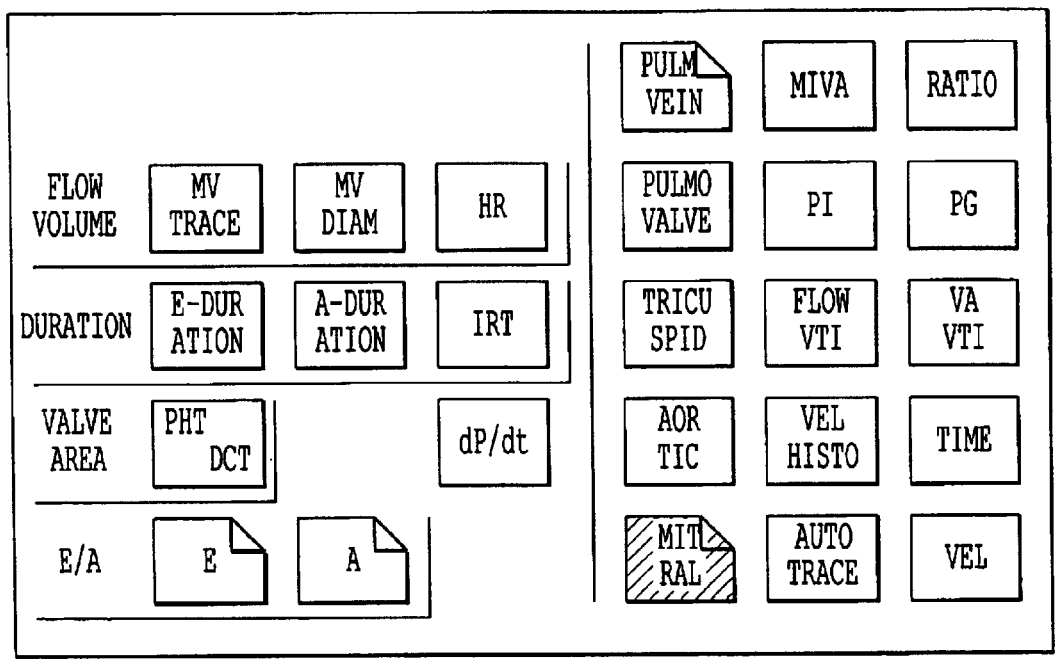
*FIG. 12*
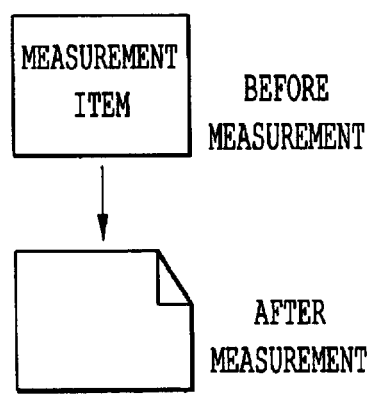
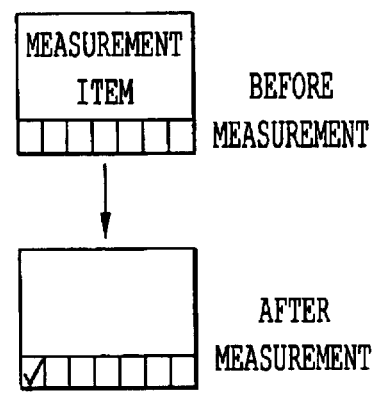
*FIG. 13A*  *FIG. 13B*

MEDICAL DIAGNOSTIC APPARATUS WITH A FUNCTION FOR PREVENTING OVERSIGHT OMISSIONS OF DATA COLLECTION ITEMS

CROSS-REFERENCE TO RELATED APPLICATIONS

This application is based upon and claims the benefit of priority from the prior Japanese Patent Application No. 2001-96671, filed Mar. 29, 2001, the entire contents of which are incorporated herein by reference.

BACKGROUND OF THE INVENTION

The present invention relates to a medical diagnostic apparatus, such as an ultrasonic apparatus or X-ray CT apparatus, having a function for preventing failure to perform all required scanning or measurements due to oversight, hereinafter called oversight omissions.

Many ultrasonic diagnostic apparatuses, in addition to obtaining and displaying an ultrasonic image of an object, employ an application program for measurements of a structural dimension such as the distance, area, volume, etc. from a B-mode image, and for measurements of a temporal variation amount from a M-mode image. An input of a direction related to such measurements with the ultrasonic diagnostic apparatus may be performed with a TCS (Touch Command Screen). Items to be measured are displayed on the TCS in a table-like form. An operator, such as a medical doctor, can input directions to the apparatus by touching on the screen a position where a desired measurement item is located. Some X-ray CT apparatuses also employ such a TCS because of its good operability, e.g. only a touch on a screen completes a desired input and items to be measured are displayed in a table-like form.

In a conventional apparatus with a TCS, to prevent oversight of omissions, items to be measured or scanned are displayed in a predetermined area on the TCS and measured values or calculated values are displayed in a window on a CRT display in a position corresponding to that on the TCS. The oversight may be prevented by the operator checking whether the measured or calculated values are displayed on the CRT display. Commonly owned U.S. Ser. No. 09/644,861 is also of interest in this regard and is incorporated by reference herein.

However, the above-mentioned function for oversight omission prevention has the following drawbacks. First, the measurement window should be displayed in the limited area on the monitor so as not to interfere with an image and a measurement marker also displayed thereon. This requires an operator to check oversights of measurement or calculation items with high attentiveness and it may also be time consuming.

Second, items with similar names are displayed in a small area. This may lead to operator misrecognition, resulting in an incomplete procedure, often in shortened form.

BRIEF SUMMARY OF THE INVENTION

It is accordingly an object of the present invention to provide a medical diagnostic apparatus, such as an ultrasonic diagnostic apparatus, capable of performing various measurements or scans of a subject, including a measuring unit configured to measure data of the subject based on a scanned image, a monitor which displays the data and the image, an input device configured to input information of the subject and an interface such as a touch command screen (TCS) for selecting measurement items. When an operator selects a switch for a desired measurement item displayed on the TCS in a first form, the measuring unit measures the selected item. When the measurement is finished, the switch is displayed in a second form different from the first form.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is an illustration of an example of items and categories to be displayed on a TCS as switches when measurement related to cardiac functions is performed, FIGS. 5(a) and 5(b) show examples of E-waves and A-waves obtained by the ultrasonic diagnostic apparatus.

FIGS. 6–12 are illustrations of examples of display patterns at various statuses in a measurement protocol of the first embodiment, FIG. 13 is an illustration of a modification of the first embodiment.

DETAILED DESCRIPTION OF THE INVENTION

Figure 1:
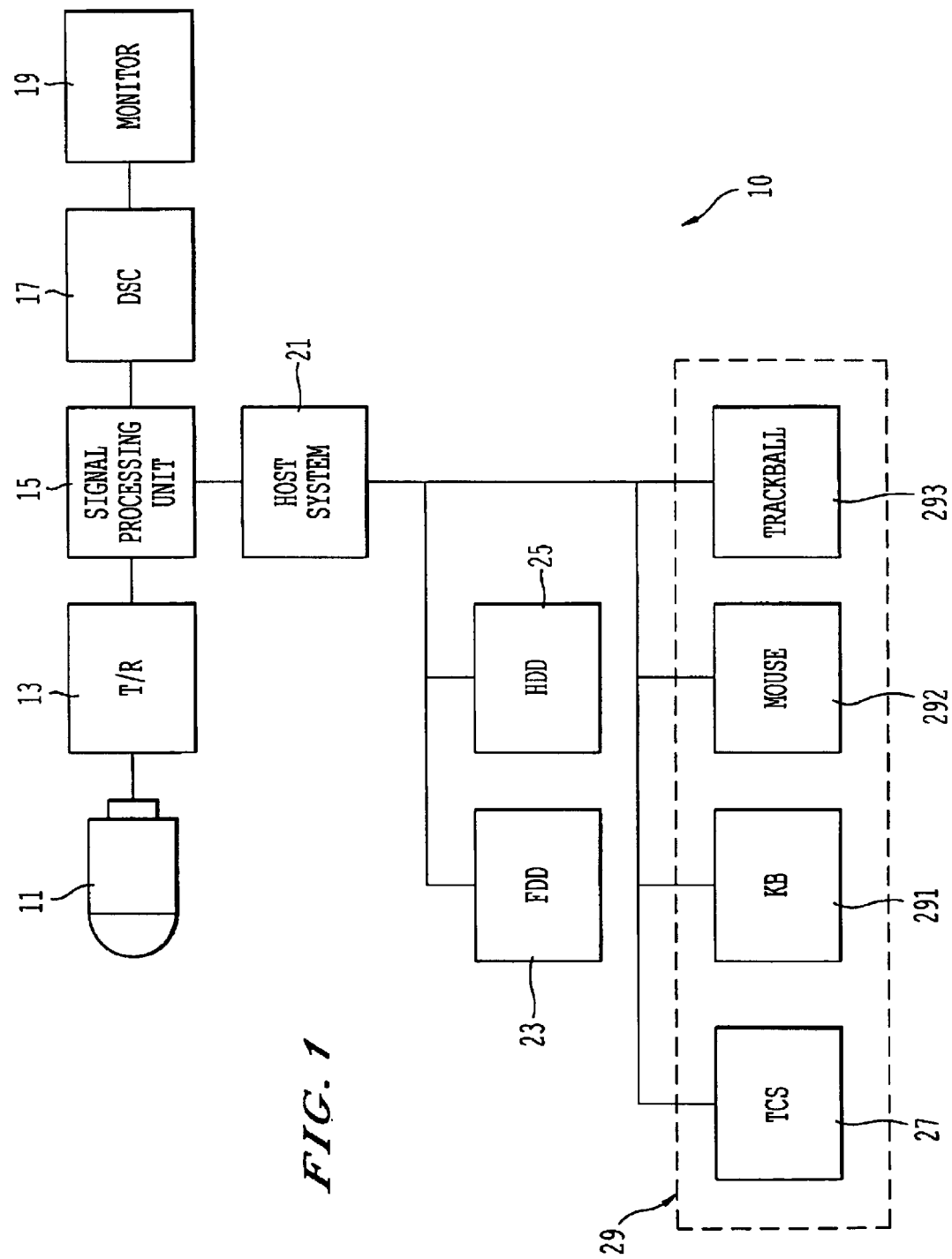
FIG. 1 shows a block diagram of an ultrasonic diagnostic apparatus of a first embodiment of the invention.

Referring now to the drawings, where like reference numeral designations identify the same of corresponding parts throughout the several reviews, several embodiments of the present invention are next described.
(First Embodiment)

The first embodiment is an example of the present invention applied to an ultrasonic diagnostic apparatus.

Figure 2:
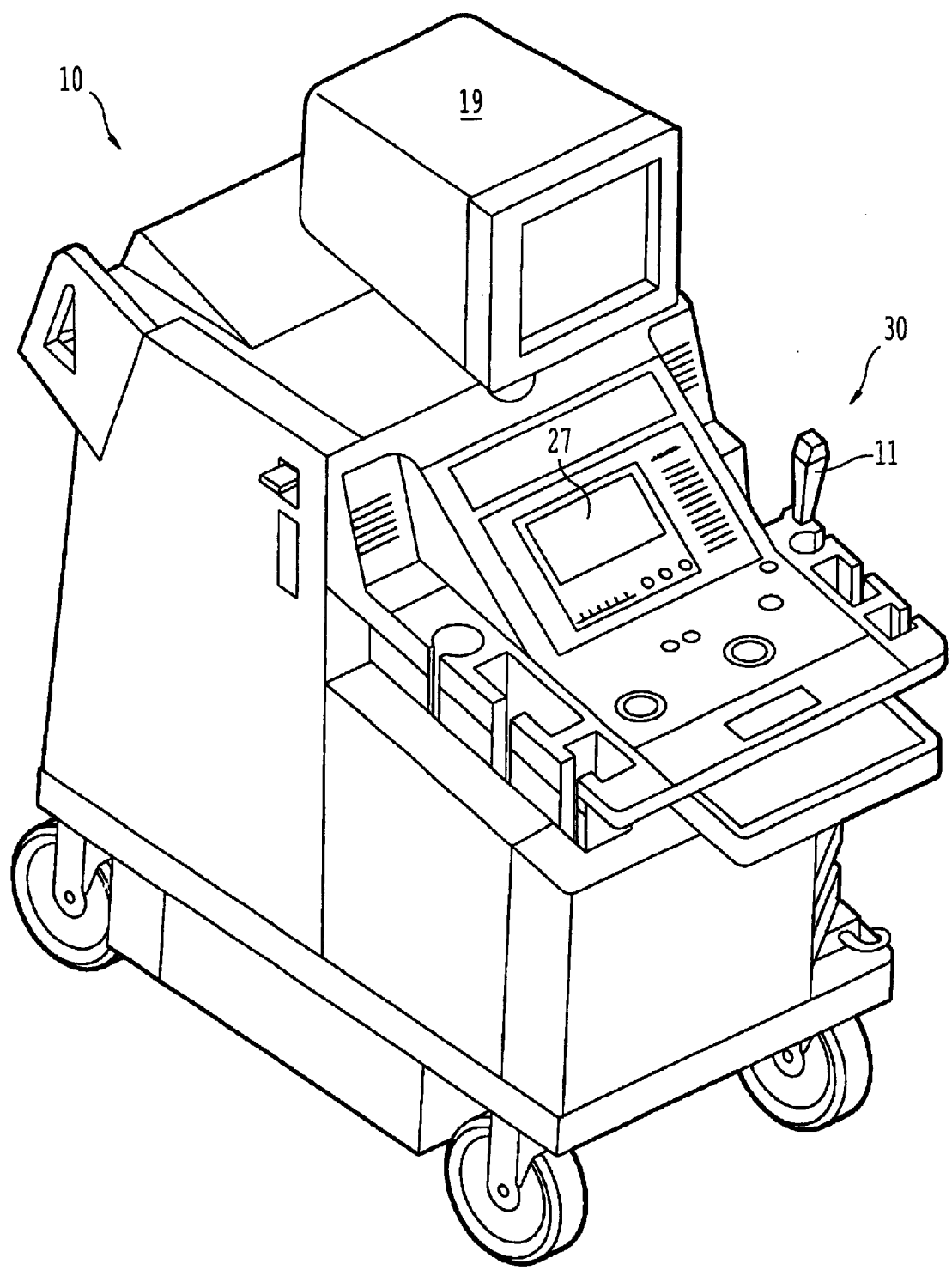
FIG. 2 is a perspective view of the ultrasonic diagnostic apparatus of the first embodiment.

FIG. 1 shows a block diagram of an ultrasonic diagnostic apparatus 10 according to the first embodiment and FIG. 2 is a schematic diagram thereof. The structure of the ultrasonic diagnostic apparatus 10 according to the first embodiment will be described referring to FIGS. 1 and 2.

The ultrasonic diagnostic apparatus 10 includes an ultrasonic probe 11, a transmitter/receiver circuit (T/R) 12, a signal processor 15, a digital scan converter (DSC) 17, a monitor 19, a host system 21, a floppy disk drive (FDD) 23, a hard disk drive (HDD) 25, a touch command screen (TCS) 27 and an input device 29.

The ultrasonic probe 11 is configured to transmit an ultrasonic wave into an object (patient) and receive the reflected wave from the object and includes piezoelectric elements, etc. The T/R 12 is connected to the probe 11 for scanning the internal body of the object with the ultrasonic wave according to a process corresponding to a desired imaging mode such as B mode representing tissue structures or Doppler mode suitable for displaying blood flow information, etc. Additionally, the T/R 12 amplifies the echo signal obtained by the scan for each channel and performs A/D conversion. The echo component from a direction corresponding to the receiving directivity is enhanced in the echo signal after A/D conversion by giving a delay time required for determining the receiving directivity and by adding. The synthesized ultrasonic beam for transmitting/receiving is formed according to the transmitting and receiving directivity. The signal processor 15 performs exponential amplification, envelope detection process and so on to the echo signal from the T/R 12 to generate data in which the signal intensity is represented by the brightness level. Further, the signal processor 15 performs frequency analysis of velocity information from the echo signal and sends the result to the DSC circuit 17.

The DSC circuit 17 stores the image signal from the T/R 12 in an image memory and sends it to the monitor 19 after TV scan conversion. Further, the DSC circuit has a function for image processing of the image data from the T/R 12 according to a desired observation condition (e.g. brightness or zooming, etc.).

The monitor 19 is a CRT monitor, for example, and displays a tomographic image representing the tissue structure of the object based on the input video signal.

The host system 21, functioning as an information processor (computer), is a controller for controlling the operations of the ultrasonic diagnostic apparatus 10. Additionally the host system 21 includes a measurement oversight omission prevention system which will be described hereinafter.

The HDD 25 is a storage device for storing desired ultrasonic image data according to a freeze command, etc. by an operator. Further, the HDD 25 reads out data stored in a hard disk, for example, a plurality of display patterns of measurement items on the TCS 27, messages such as names of the measurement items to be superimposed on the display patterns, font data related to the TCS 27 display and a table relating the measurement items displayed on the TCS 27 with specific operations of the ultrasonic diagnostic apparatus 10. The FDD 23 is a driver for reading out data stored in an inserted auxiliary storage device (floppy disk). Some of data stored in the HDD 25 as described above may be stored in the FDD 23 instead.

The TCS 27 is a contact panel for the operator to select and direct an operation of a measurement item to be performed in ultrasonic diagnosis. As shown in FIG. 2, the TCS is arranged on the console part 30 of the ultrasonic diagnostic apparatus 10. On this TCS 27 selection elements or switches corresponding to measurement items are displayed in an array. By contacting a switch for a desired measurement item, the operator can input a direction to operate the item. Further, the TCS 27 displays the measurement items in a format according to the measurement oversight omission prevention system to be described hereinafter.

The input device 29 is a device for the operator to input various directions, commands, or information and may include a keyboard 291, a mouse 292 and a trackball 293. Some of the information may be input or transferred through a network system connected to a separate computer or the other medical diagnostic apparatus.

Figure 3:
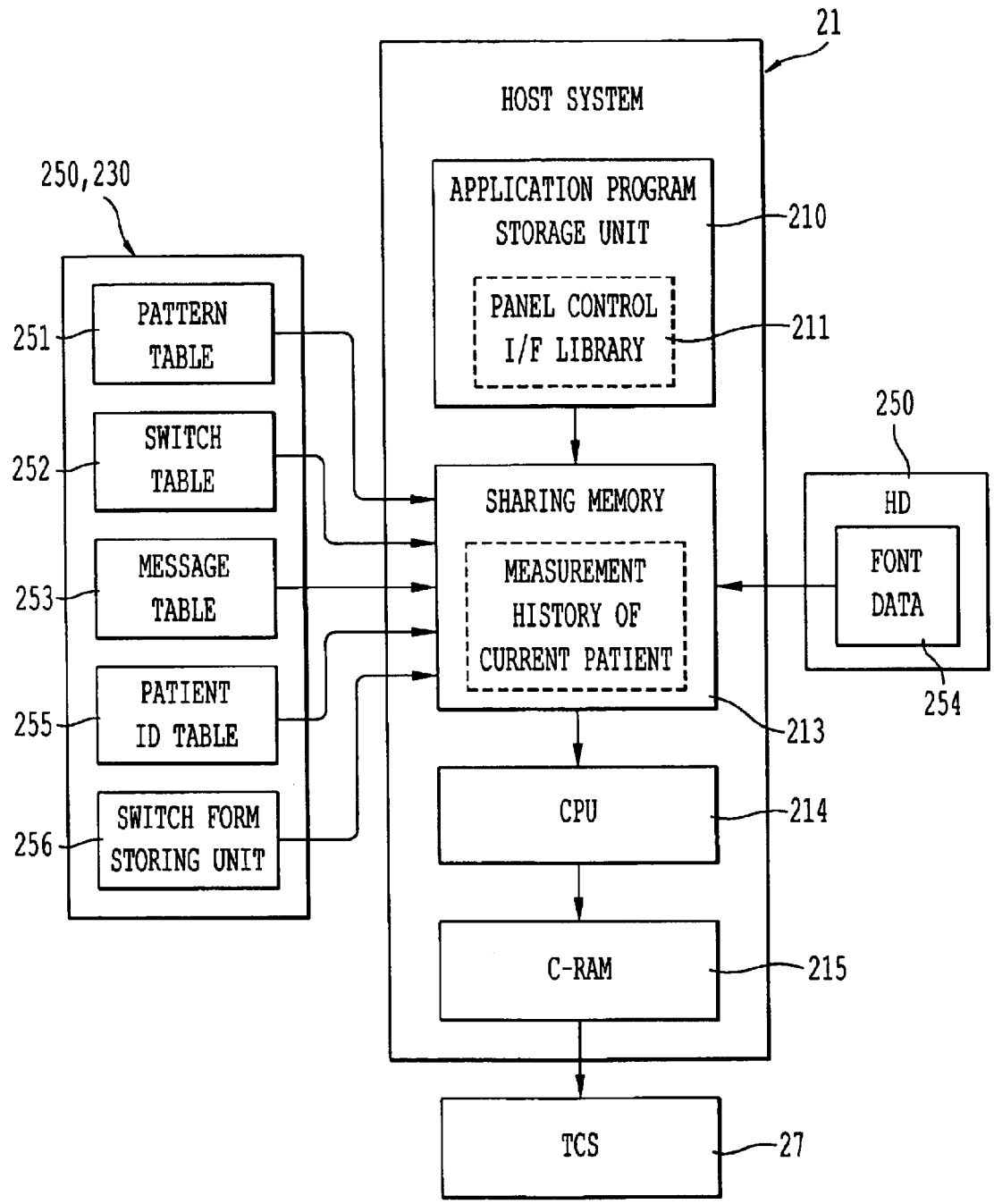
FIG. 3 is a block diagram of a measurement oversight omission prevention system of the first embodiment.

Next, the measurement oversight omission prevention system will be described below. This system controls the display format of the measurement items on the TCS 276 and is included in the host system 21. FIG. 3 is a block diagram of the measurement oversight omission prevention system, which will be described based on the diagram.

The measurement oversight omission prevention system includes an application program storing unit 210, a sharing memory 213, a CPU 214, a C-RAM 215 and a font data storing unit 254 provided in the host system 21 and a pattern table storing unit 251, a switch table storing unit 252, a message storing unit 253, a patient ID table storing unit 255 and switch form storing unit 256 provided in the HD 250 or the FD 230. Each of these elements will be described below.

The font data storing unit 254 stores font data for various languages (e.g. Japanese, English, German, etc.) related to the items displayed on the TCS 27. The operator can select one of these languages with the input device 29. The patient ID table storing unit 255 stores a patient ID table, which is already created by the operator or a doctor who examines the patient, defining combinations of patient ID numbers and measurement protocol pattern numbers. The patient ID table may be created by a separate computer system in the FD 230 to be inserted in the FDD 23 or it may be transferred from the computer system into the HD 250 through a network system. The pattern table storing unit 251 stores a pattern table including data of switch patterns to be displayed at the initial status of the TCS 27, each of switch patterns corresponding to one of the measurement protocol pattern numbers. When the operator inputs information of a patient, e.g. patient ID number, from the keyboard 291, the measurement protocol to be used for the patient is determined based on the patient ID table in the patient ID table storing unit 255, a switch pattern corresponding to the measurement protocol is read out from the pattern table in the pattern table storing unit 251 and displayed on the TCS 27. Because the displayed switch pattern is based on the measurement protocol corresponding to the patient ID, only the switches necessary for the patient is displayed or activated on the TCS 27.

The switch table storing unit 252 stores a table defining relationships between each of the switches of the switch patterns and a function of the ultrasonic diagnostic apparatus 10. The CPU 214 performs the measurement corresponding to the selected switch by referring to this table.

The message table storing unit 253 stores data of names for the switches of the switch pattern table and the data is referred to when the switch pattern data is read out. The switch form storing unit 256 stores data of the forms of the switches to be displayed on the TCS 27. The switch forms include at least two patterns of the switches, i.e. patterns for before/after the measurement is finished, and each pattern may define the shape, color or size of the switches.

The application program storing unit 210 is provided in the HD 250 and stores various application programs. The measurement oversight omission prevention system is performed according to a panel control program stored in a panel control interface library 211 in the unit 210.

The sharing memory 213 is a main memory device for temporarily storing a program necessary for running the system or various data to be used and for transferring the program and/or data to the CPU 214. Specifically, it temporarily stores the panel control program read out from the application program storing unit 210, various information read out from the pattern table storing unit 251 in the HD 250 or the FD 230 or a past measurement record related to the currently performing examination. The CPU 214 controls the display on the TCS 27 by executing the panel control program according to a predetermined task control block. The RAM 215 is a memory device for temporarily storing display data to be displayed on the TCS 27. The contents of the RAM 215 are rewritten from time to time by the CPU 214 as the progress of the measurements. Newly written contents are displayed on the TCS 27.

Next, the display method of measurement items for ultrasonic diagnosis according to the measurement oversight omission prevention system having a structure as shown above will be described.

FIG. 4 is a table showing measurement categories available for ultrasonic diagnosis of cardiac function and switches to be displayed in a measurement menu for each measurement category. Detailed explanations for each measurement items are omitted here and an example of performing measurements of E-wave and A-wave (measurements when switches [E] and [A] are selected) in the MITRAL category (mitral valve function measurement) will be described. An E-wave is a blood flow waveform observed at the early ventricle diastolic phase in Doppler method, while an A-wave is at the atrium systolic phase. By obtaining blood flow velocity, time information (e.g. duration, acceleration time, deceleration time, or isovolumic relaxation time), blood flow acceleration or blood flow deceleration, etc., various ventricle relaxation capabilities can be evaluated.

FIGS. 5(a) and 5(b) show blood flow waveforms at mitral valves of a healthy young subject and a hypertension subject, respectively. These A-and E-waves of each subject show that the E-wave is higher than the A-wave of the healthy young subject as shown in FIG. 5(a), while the A-wave is higher than the E-wave for the hypertension subject. The decrease of the E-wave of the hypertension subject indicates that the left ventricle isovolumic relaxation is prolonged and the increase of the A-wave indicates compensatory hypertrophy.

Next, the display examples for preventing measurement oversight performed in the E-and A-wave measurements will be explained. In this example, the operator is supposed to perform E-and A-wave measurements in the mitral category and S1, S2 and D measurements in the pulmo vein category according to the predetermined protocol.

FIG. 6 is an example of a display pattern initially displayed on the TCS 27 during the ultrasonic cardiac function diagnosis. This pattern is displayed following an input of a patient ID number to determine the measurement protocol corresponding to a switch pattern for measurements related to cardiac function. In FIG. 6 every switch is displayed in the same shape because no measurements related to ultrasonic diagnosis has been performed at this time. Such a display status is called an "initial status" hereinafter. Switches for measurement items or categories not included in the selected protocol may not be activated (shown in a different form, e.g. pale color or broken-lined outline) or may not be displayed.

First, the operator, such as a doctor or an examination technician, presses a "MITRAL" switch displayed on the TCS 27. Responding to this action, the CPU 214 commands the "MITRAL" switch to change its color or to display it as a negative image. The operator can easily realize that the "MITRAL" measurements are currently being performed. In the left part of the screen a menu for the measurement items included in the "MITRAL" category is displayed.

Figure 7:
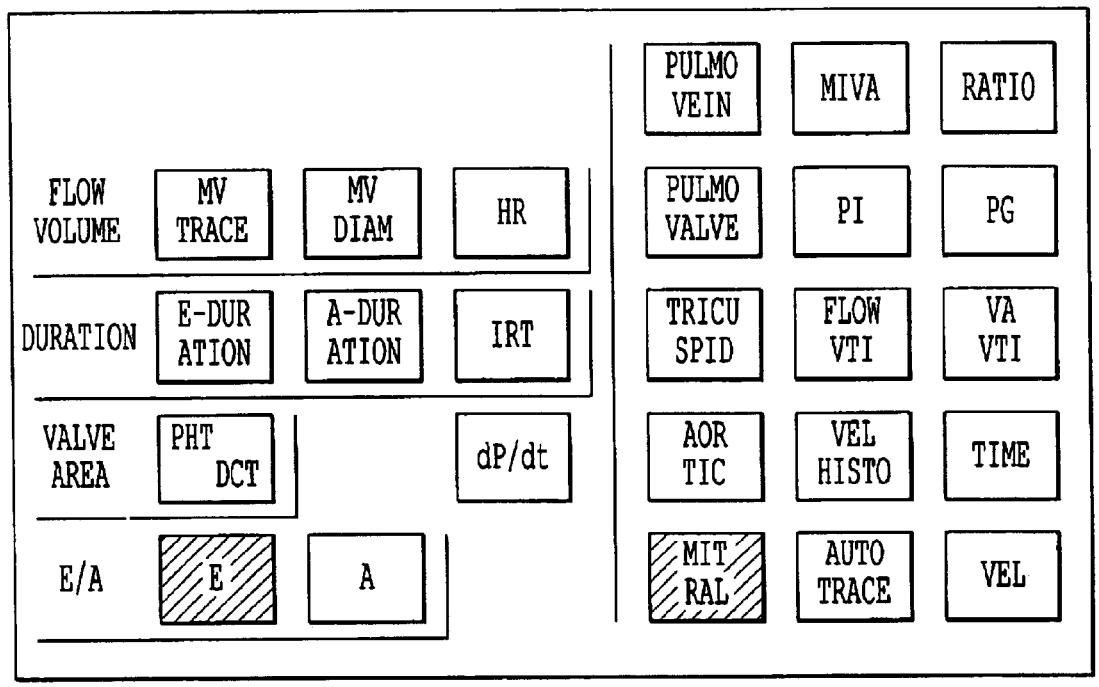

Then the operator touches the "E" switch displayed on the TCS 27. Responding to this action, the CPU 214 commands the "E" switch to be negative and starts measurement of the E-wave. The negative display of the "E" switch is maintained throughout the E-wave measurement as shown in FIG. 7.

When the CPU 214 finishes measurement of the E-wave, it adds the fact of finishing the E-wave measurement in the measurement history of the current patient in the sharing memory 213. The CPU 214 also rewrites information of the "E" switch in the RAM 215 to change its form into that showing the finish of the measurement as shown in FIG. 8.

Figure 8:
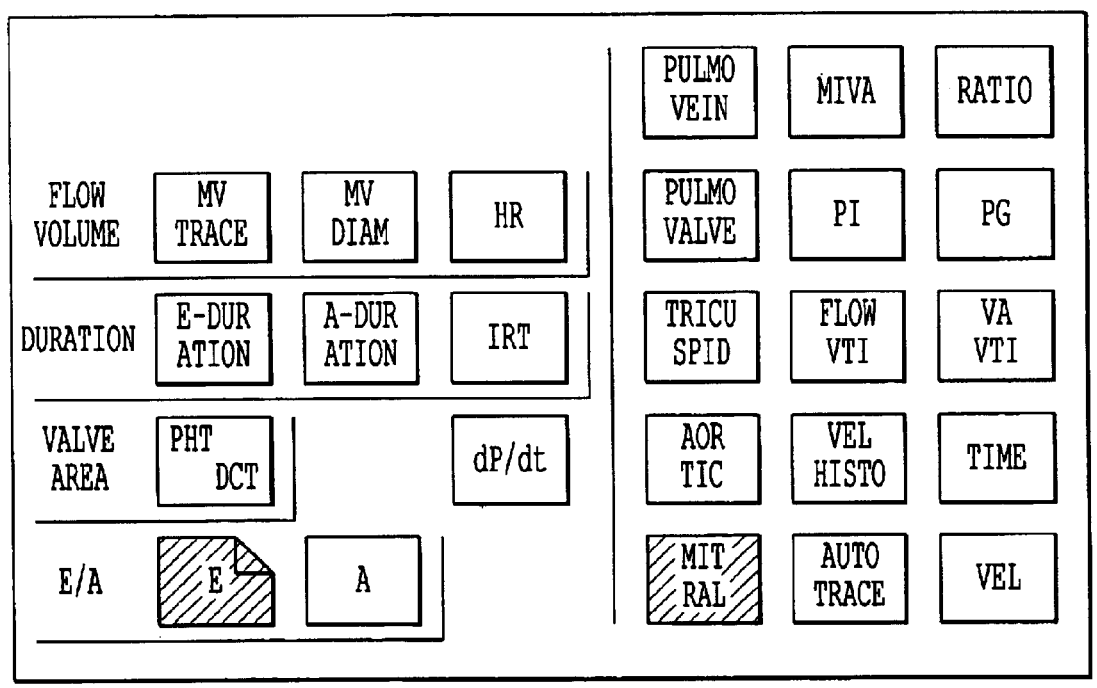
Figure 9:
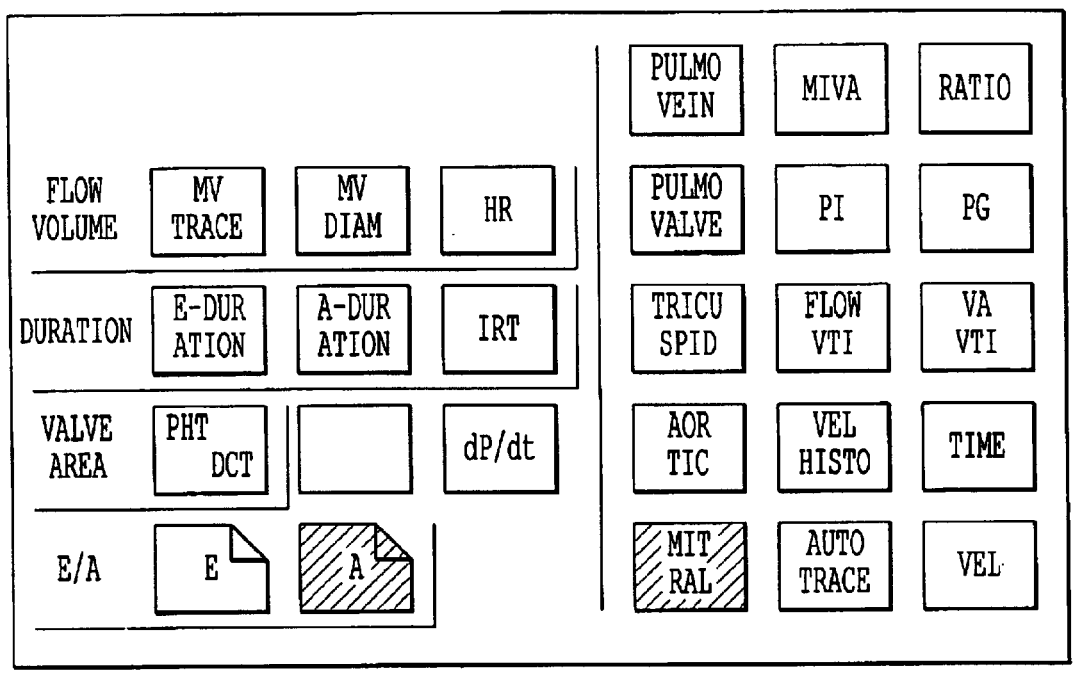

As shown in FIG. 8, one of the corners of the displayed "E" switch is folded in the display to indicate, based on this change in displayed form, that the measurement has been completed. However, other visible changes in form are possible, as long as the changes in form are readily observable and noticeable by the operator. Changes in color are also useful for this purpose. Further, the CPU 214 sends data of the measurement result to be displayed on the monitor 19 and returns the "E" switch to be normal from the negative image. Similarly the A-wave measurement is performed and when it finishes, the CPU 214 changes the form of the "A" switch into that shown in FIG. 9.

According to the changes of the display form of the switches, the operator can realize at a glance that the E-and A-wave measurements in the mitral measurement category are finished. In the conventional apparatus in which the finish of measurement is not reflected on the display form of the switch, the screen would be displayed as shown in FIG. 6 when the A-wave measurement is finished. Therefore when the operator forgets whether the E-wave measurement is finished, he or she must check with the measurement result on the monitor 19 or print out a report, which is hard to be completed in a short time. This would result in the whole measurement taking a long time.

On the contrary, according to the ultrasonic diagnostic apparatus 10 of this embodiment, the completion of the measurements can be visually confirmed with ease simply by observing a change in form of the respective selection switch displayed on the TCS. As a result, the operator would not make a mistake in confirming whether the measurements are finished and realize the status.

Figure 10:
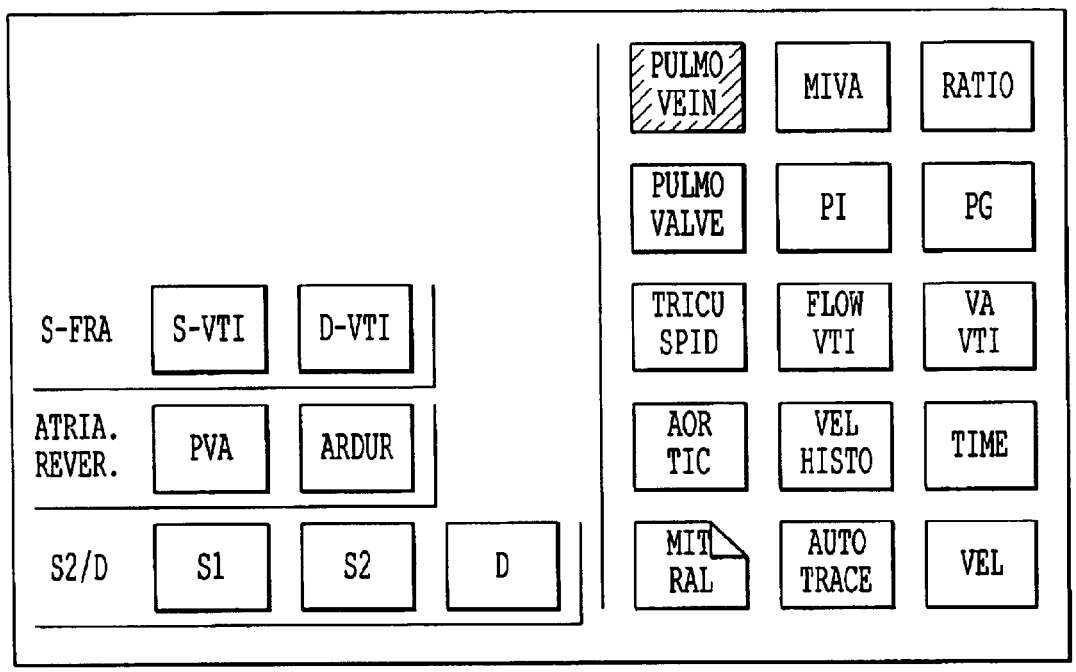

Since the mitral category consists of E-and A-wave measurements in this embodiment, the "MITRAL" switch also changes its form to that reflecting the finish of the measurement when the measurement of the A-wave is finished as shown in FIG. 10. Then, when the operator moves to the category of the pulmo vein function measurement, he or she selects the "PULMO VEIN" switch. Responding to the selection of the switch, the CPU 214 turns the "PULMO VEIN" switch into a negative image and reads out the switch pattern corresponding to the pulmo vein measurement and names of required items to be displayed on the switches from appropriate storage units in the HD 250 or FD 230.

FIG. 10 shows a display example on the TCS 27 when the "PULMO VEIN" is selected. According to this figure, the display control and form when pulmo vein function measurements "S1", "S2" and "D" are performed will be described.

Figure 11A:
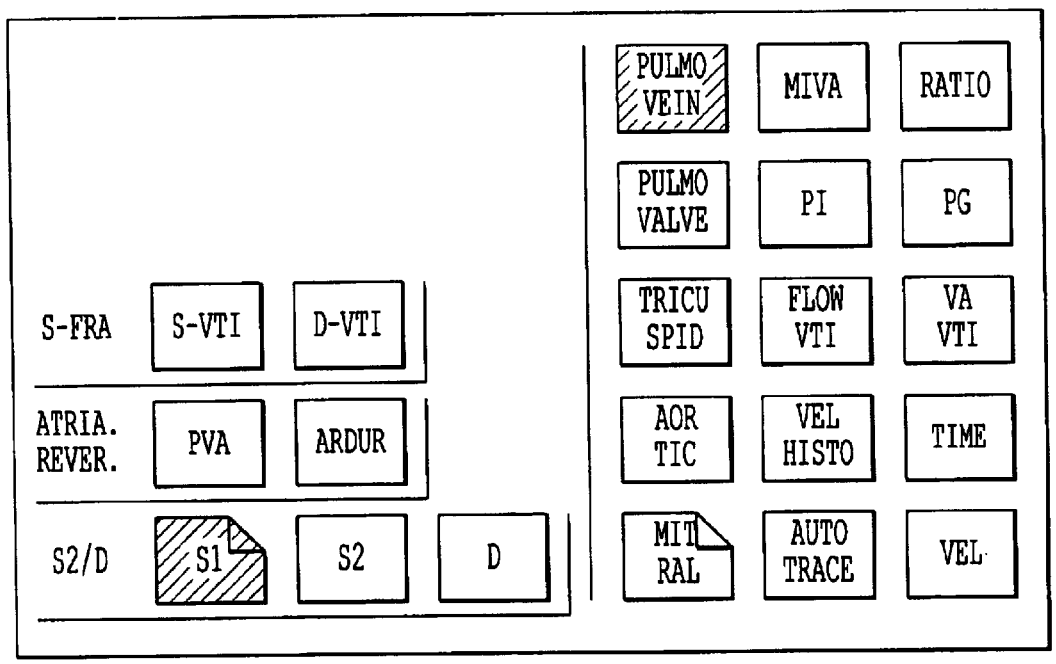

When the operator selects the switch "S1" displayed on the TCS 27, the CPU 214 turns the switch into negative and starts the measurement. The negative image of the switch "S1" is maintained throughout the S1 measurement. When the CPU 214 finishes the S1 measurement, it adds the fact of finishing the S1 measurement in the measurement history of the current patient in the sharing memory 213. The CPU 214 also rewrites information of the "S1" switch in the RAM 215 to change its form into that showing the finish of the measurement as shown in FIG. 11(a). Further, the CPU 214 sends data of the measurement result to be displayed on the monitor 19 and returns the "S1" switch to be normal from the negative image. Similarly the S2 and D measurements are selected and performed one after another and when each of them finishes, the CPU 214 changes the form of the corresponding switch. When all of the measurements are finished in the "PULMO VEIN" category, the TCS 27 displays a screen as shown in FIG. 11(b).

Figure 11B:
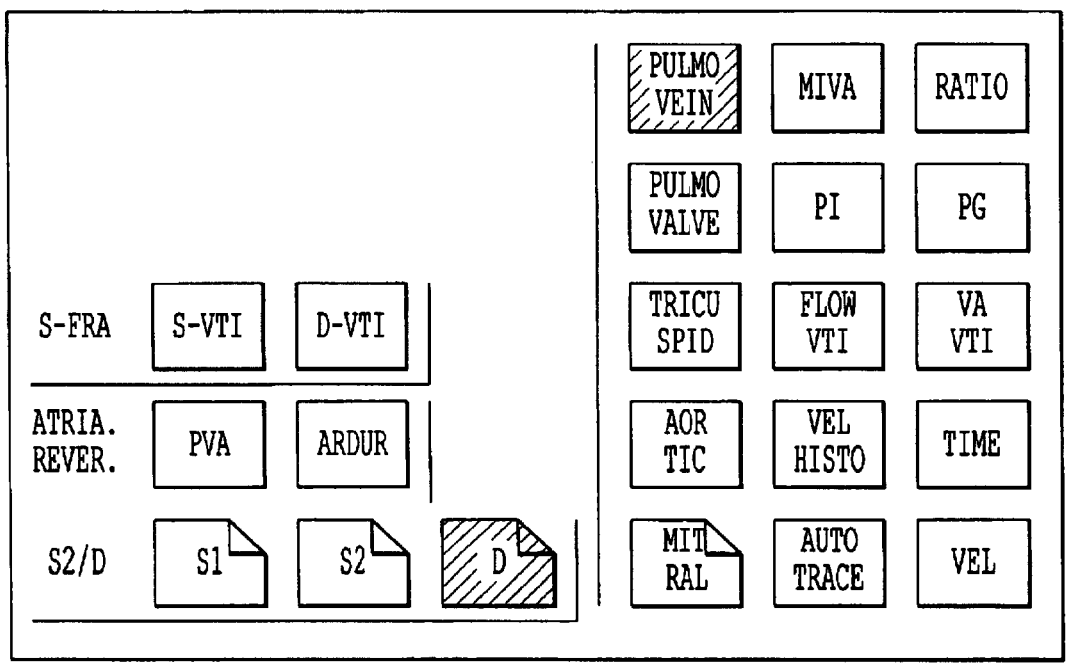

When the operator wants to check whether the E-and A-wave measurements in the "MITRAL" category at the status of FIG. 11(b), the measurement items corresponding to the "MITRAL" can be displayed as shown in FIG. 12 by pressing the switch "MITRAL" in the cardiac function menu. In this status of the screen, the switches corresponding to the measurement items "E" and "A" are displayed in the form indicating that the measurements are finished. Therefore, the operator can confirm whether a measurement is finished at any time. As a result, the work load of the operator is reduced and oversights in the procedure can be prevented.

On the contrary, in the conventional ultrasonic diagnostic apparatus, when the switch "MITRAL" in the cardiac function measurement menu at the status of FIG. 11(b) is pressed, a pattern similar to the initial status as shown in FIG. 6 would be displayed. Therefore, the operator can not confirm whether the measurement is finished on the TCS 27 and he or she must check with the measurement result on the monitor 19.

The form indicating completion of the measurement may be any form as long as the operator can readily realize the change in form indicating completion of the measurement. For example, the shape of the switch may change in a manner other than that shown in FIGS. 8–11, or the color or size of the switch may change. Otherwise, a double line may be overlaid, e.g., around a periphery of the finished measurement switch, or a predetermined symbol such as a large "X" may be alternatively overlaid.

In addition, the display form showing of the finished measurement is maintained until the operator inputs a direction to reset, such as pressing a reset button (not shown) on the console, etc. Unless such a reset action is performed, the operator can easily realize the measurement history in the current examination during the ultrasonic diagnosis. Furthermore, the form showing the measurement finish may be automatically reset at the timing that the next patient is set. The automatic recognition of the new patient may be achieved by inputting his or her patient ID number.

Next, a modified embodiment of the above will be explained. In ultrasonic diagnosis, the same measurement is often repeated a plurality of times to obtain a mean value of the measured values. For example, in the measurement of the A-and E-waves, a mean spectrum obtained from several measurements is often used for ultrasonic diagnosis. The following modified embodiment is especially beneficial when repeating the same measurement a plurality of times for the same patient.

FIGS. 13(a) and 13(b) explain a modification of the first embodiment. In the first embodiment as described above, whether the measurement is finished is recognized by changing the display form as shown in FIG. 13(a). On the other hand, in this modified embodiment, a switch may be displayed in a format by which the number of repetitions of the measurements can be recognized as shown in FIG. 13(b). As shown in FIG. 13(b), a mark appears on the switch every time the measurement is finished. The operator can recognize the number of the finished measurements by counting the marks. The display form in this modification of the first embodiment is not limited to the above-mentioned example but it may be any form as long as it shows the number of repetitions of the measurements. For example, it may show a numerical figure or symbolic figure representing the number of the finished measurements. Further, it is desirable that the shape of the switches changed after the measurements or the number shown on the switch is automatically reset every time a new patient is set according to, for example, an input of the patient ID. This can be achieved by the CPU 214 resetting the current measurement history and displaying on the TCS 27 the initially status in response to the input of the patient ID from the keyboard 291 or by restarting the measurement oversight omission prevention system. With these features the operator does not have to manually reset the TCS 27 when a new patient is set and the efficiency of the operation is improved.

According to the above-mentioned first embodiment, the operator can easily and rapidly make a visual confirmation of whether the measurements are finished or the number of the measurements finished based on changing the form of the switches of the measurement items or categories displayed on the TCS 27. Therefore, the operator can operate the measurements without fail in recognizing which measurements are completed.

Additionally, among other medical diagnostic apparatuses the above-mentioned display manner is especially useful for an ultrasonic diagnostic apparatus. Usually an ultrasonic diagnostic apparatus does not store all the scanned images and it is difficult for the operator to perform the measurements without a patient being set in front of the apparatus. Therefore, an efficient operation as achieved by this embodiment is extremely significant.

(Second Embodiment)

The second embodiment is an example of the present invention applied to an X-ray CT apparatus.

Figure 14:
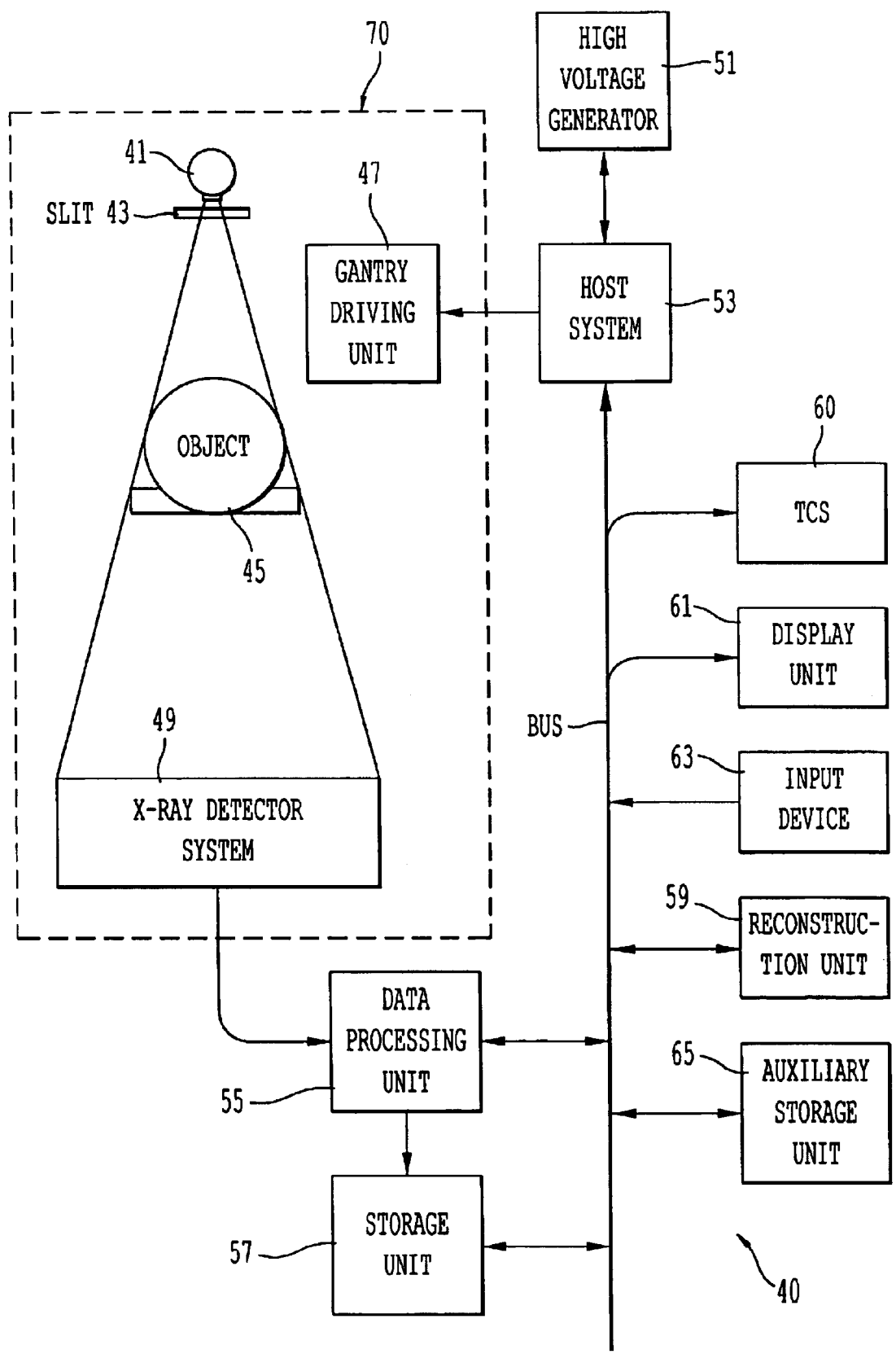
FIG. 14 is a block diagram of an X-ray CT apparatus of a second embodiment of the invention.

FIG. 14 shows a block diagram of an X-ray CT apparatus 40 according to the second embodiment. The X-ray CT apparatus comprises a gantry 70 (surrounded by a broken line) for obtaining projection data of the object and a main system (outside the broken line) for processing image reconstruction and displaying the reconstructed image based on the obtained projection data.

The gantry 70 includes an X-ray tube 41, a slit 43, a couch 45 for positioning the object, an opening (not shown) for inserting the object, a gantry driving unit 47 and an X-ray detector system 49. The X-ray tube 41 is a vacuum tube for generating X-rays by hitting a target with electrons accelerated by high voltage generated by a high voltage generator 51. The slit 43 is provided between the X-ray tube 41 and the object P for shaping the X-ray bean emitted from the X-ray tube into a cone or fan shape to form an X-ray beam with a desired angle. The couch 45 is slidable along the body axis of the patient P by a couch driving unit (not shown). The gantry driving unit 47 controls such that the X-ray tube 41 and the X-ray detector system 49 rotate together around the body axis of the patient P inserted in the opening. The X-ray detector system 49 transfers a plurality of current signals of projection data detected by scanning to a data processing unit 55.

The main system 49 comprises the high voltage generator 51, a host system 53, the data processing unit 55, a storage device 57, a reconstruction unit 59, a TCS 60, a display unit 61, an input device 63 and an auxiliary storage unit 65. The high voltage generator 51 supplies high voltage to the X-ray tube 41 including a high voltage transformer, a filament heating converter, a rectifier and a high voltage switching unit. The high voltage from the high voltage generator 51 may be supplied to the X-ray tube 41 through a slip ring mechanism.

The host system 53 includes a computer having a CPU and is connected to the high voltage generator 51 and also connected through a bus B to the couch driving unit, the gantry driving unit 47 and the X-ray detector system 49. The host system 53, the data processing unit 55, the storage unit 57, the reconstruction unit 59, the TCS 60, the display unit 61, the input device 63 and the auxiliary storage unit 65 are respectively connected through the bus B and they rapidly transfer image data or control data to one another. The host system 53 stores information, such as imaging conditions, input from the TCS 60 or the input device 63 in an internal memory, controls each unit according to the information and executes an X-ray CT scan. The host system 53 also includes a scan oversight omission prevention system which will be described later.

The data processing unit 55 including a computer with a CPU, etc. holds projection data for 32 slices collected by detector elements in the X-ray detector system 49. The data processing unit 55 further performs various processes, such as adding all the projection data for the same slice obtained at a plurality of angles made by the gantry driving unit 47 and interpolating and correcting of the multiple angle data obtained by the adding process if necessary.

The storage unit 57 stores data necessary for the data processing at the data processing unit 55. For example, it stores a plurality of display patterns for scan items to be displayed on the TCS 60, messages such as names of the scan items to be superimposed on the display patterns, font data related to the TCS 27 display and a table relating the scan items displayed on the TCS 27 with specific operations of the X-ray CT apparatus 40. The reconstruction unit 59 reconstructs the projection data processed by the data processing unit 55 to produce reconstructed image data for the predetermined number of slices.

The TCS 27 is a contact panel for the operator to select and direct an operation of a scan item to be performed in X-ray CT scanning. On this TCS 27 switches corresponding to scan items are displayed in an array. By contacting a switch for a desired scan item, the operator can input a direction to operate the item. Further, the TCS 27 displays the measurement items in a format according to the scan oversight omission prevention system to be described hereinafter. The input device 29 may include a keyboard 291, a mouse 292 and a trackball 293 for the operator to input various scan conditions such as slice thickness and the number of slices, etc. The auxiliary storage unit 65 has a storage area with a large capacity capable of storing reconstructed image data produced by the reconstruction unit 59.

Figure 15:
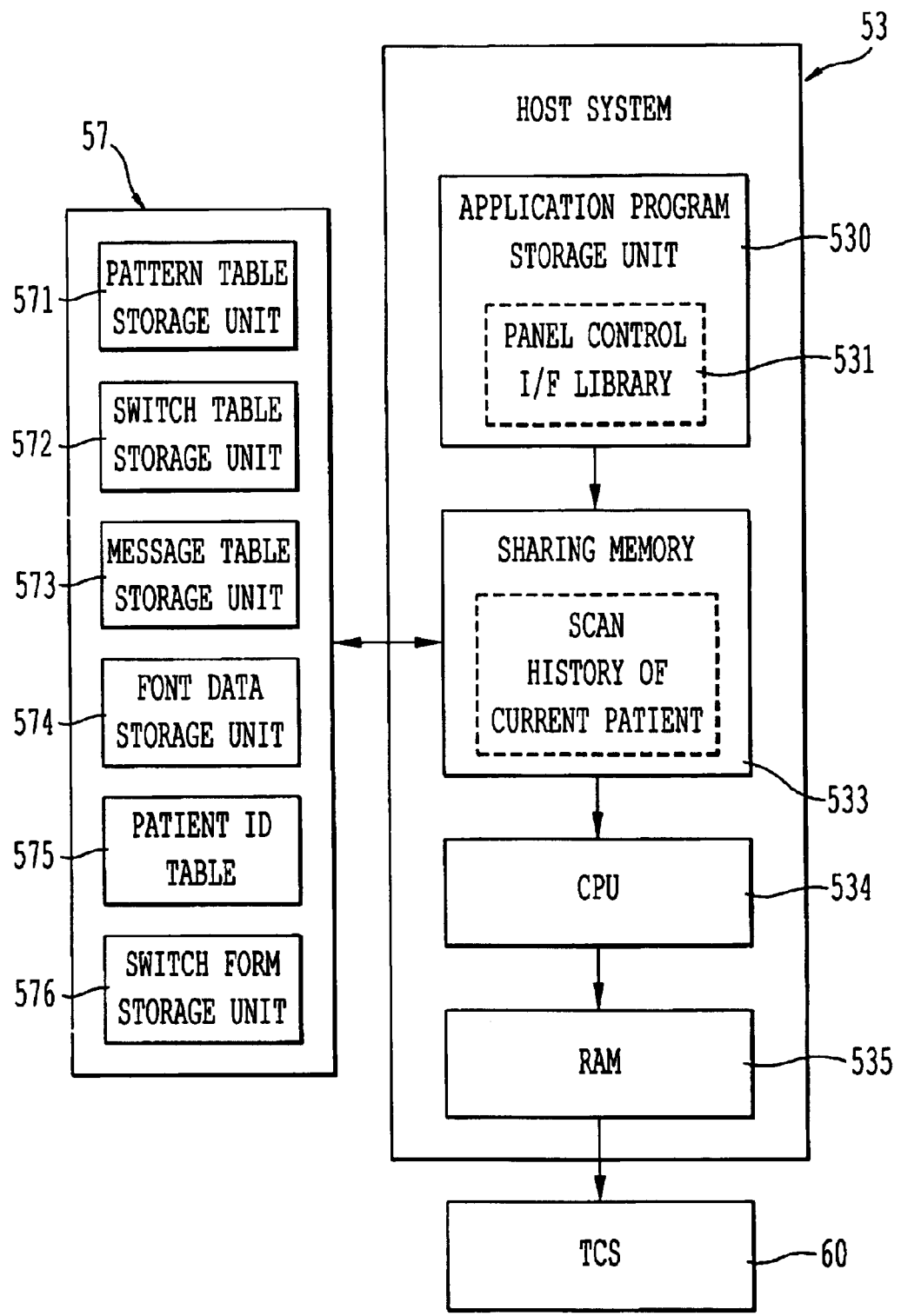
FIG. 15 is a block diagram of a scan item oversight omission prevention system of the second embodiment.

Next, the scan oversight omission prevention system will be described below referring to FIG. 15 showing a block diagram of the system. The scan oversight omission prevention system is constituted by the host system 53 including an application program storing unit 530, a sharing memory 533, a CPU 534, a RAM 535 and the storage unit 57 including a font data storing unit 574, a pattern table storing unit 571, a switch table storing unit 572, a message storing unit 573, a patient ID table storing unit 575 and switch form storing unit 576. Each of these elements will be described below.

The font data storing unit 574 stores font data for various languages (e.g. Japanese, English, German, etc.) related to the items displayed on the TCS 60. The operator can select one of these languages with the input device 63. The patient ID table storing unit 575 stores a patient ID table, which is already created by the operator or a doctor who examines the patient, defining combinations of patient ID numbers and scan protocol pattern numbers. The patient ID table may be created by a similar manner as described for the first embodiment of the invention. The pattern table storing unit 571 stores a switch pattern table defining switch patterns to be displayed at a default status (prior to start a scan), each of switch patterns corresponding to one of the scan protocol pattern numbers. When the operator inputs information of a patient, e.g. patient ID number, from the keyboard, the scan protocol to be used for the patient is determined based on the patient ID table in the patient ID table storing unit 575, a switch pattern corresponding to the scan protocol is read out from the pattern table in the pattern table storing unit 571 and displayed on the TCS 60. Because the displayed switch pattern is based on the scan protocol corresponding to the patient ID, only the switches necessary for the patient are displayed or activated on the TCS 60.

The switch table storing unit 572 stores a table defining relationship between each of the switches of the switch patterns and a function of the X-ray CT apparatus. The CPU 534 performs the scan corresponding to the selected switch by referring to this table. The message table storing unit 573 stores data of names for the switches of the switch pattern table and the data is referred to when the switch pattern data is read out. The switch form storing unit 576 stores data of the forms of the switches to be displayed on the TCS 60. The switch forms include at least two patterns of the switches, i.e. patterns for before/after the scan is finished, and each pattern may define the shape, color or size of the switches.

The application program storing unit 530 stores various application programs. The scan oversight omission prevention system is performed according to a panel control program stored in a panel control interface library 211 in the unit 530. The sharing memory 213 is a main memory device for temporarily storing a program necessary for running the system or various data to be used and transferring to the CPU 534. Specifically, it temporarily stores the panel control program read out from the application program storing unit 530, various information read out from the pattern table storing unit 571 in the storage unit 57 or a past scan record related to the currently performing examination. The CPU 534 controls the display on the TCS 60 by executing the panel control program according to a predetermined task control block. The RAM 535 is a memory device for temporarily storing display data to be displayed on the TCS 60. The contents of the RAM 535 is rewritten from time to time by the CPU 534 as the progress of the measurements. Newly written contents are displayed on the TCS 60.

Next, the display method of scan items for X-ray CT apparatus according to the scan oversight omission prevention system having a structure as shown above will be described.

Figure 16:
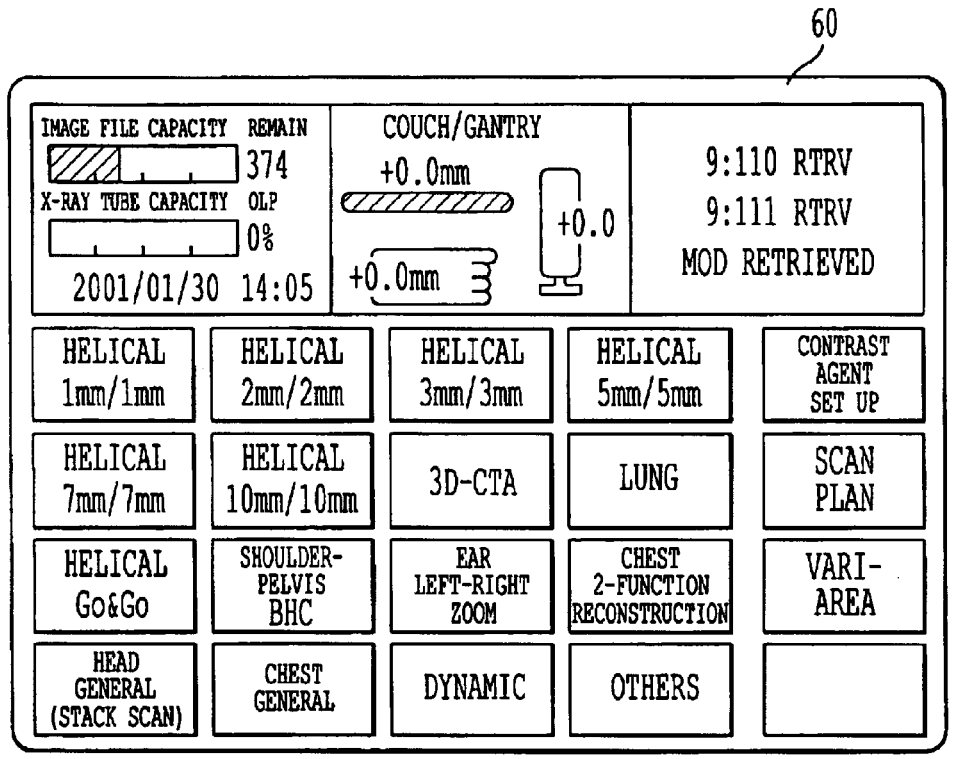
FIGS. 16–18 show examples of display patterns at various statuses in a scan protocol of the first embodiment.
Figure 17:
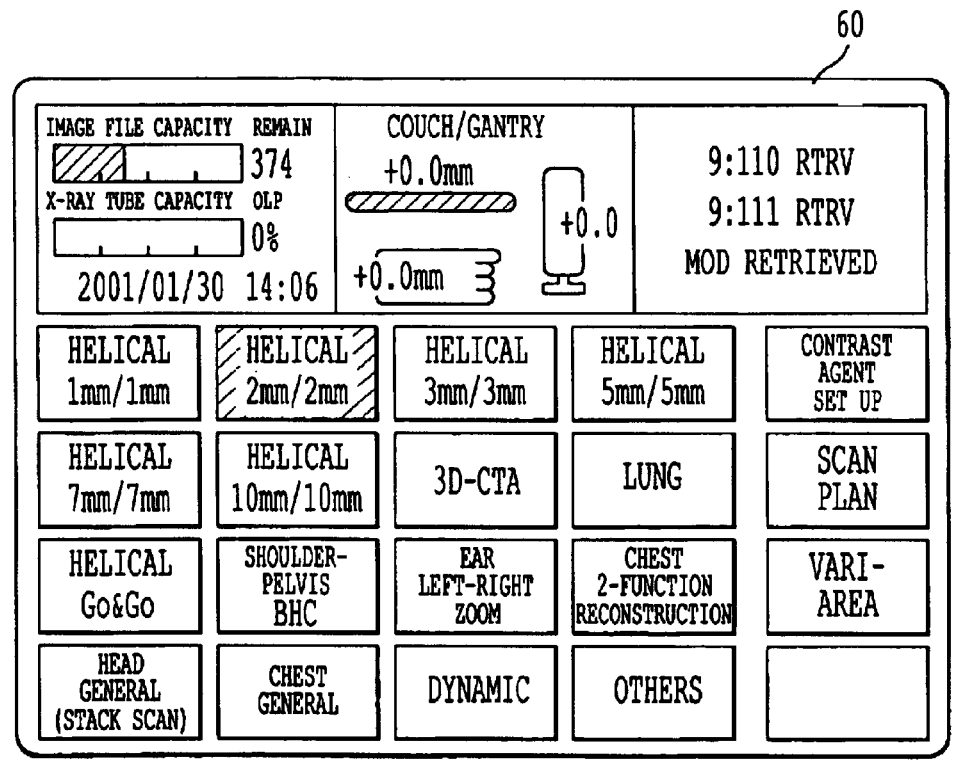

FIG. 16 is an example of a display pattern of the TCS 60 at the initial status. As shown herein, the TCS 60 displays various scans to be performed by the X-ray CT as buttons to select. For example, when a 2 mm/2 mm helical scanning is performed for a patient, at first the operator, such as a doctor or a technician, presses a "HELICAL 2 mm/2 mm" switch displayed on the TCS 60. Responding to this action, the CPU 534 commands the "HELICAL" switch to change its color or display it as a negative image. The operator can easily realize that the "HELICAL 2 mm/2 mm" scan is currently performed.

Figure 18:
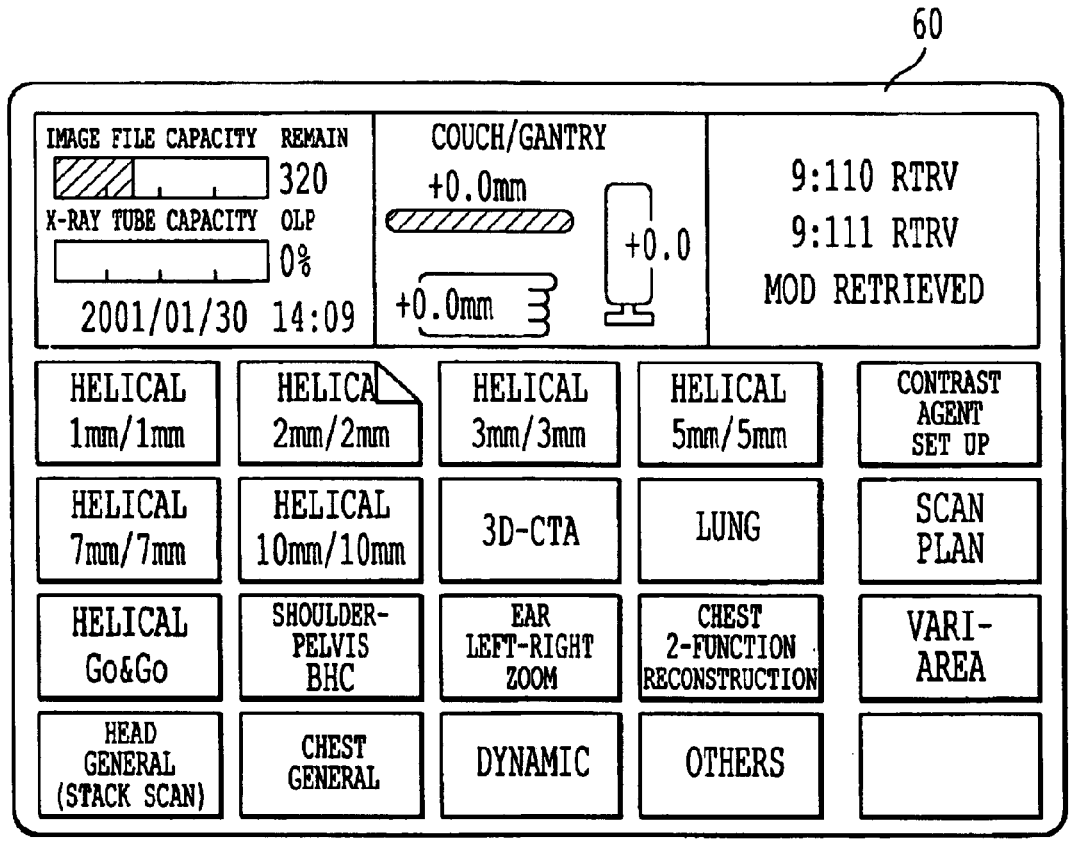

When the 2 mm/2 mm helical scan finishes, CPU 534 writes the fact of finishing the scan as "measurement history of the current patient" in the sharing memory 533. The CPU 534 also rewrites information of the "HELICAL 2 mm/2 mm" switch in the RAM 535 and changes its form into that showing the finish of the scan as shown in FIG. 18. Further, the CPU 534 returns the "HELICAL 2 mm/2 mm" switch to be normal from the negative image. When the other scan is performed according to the predetermined scan protocol, the displaying manner of the switches is similarly controlled according to the scanning status.

According to the above-mentioned embodiment, the operator can easily and rapidly make a visual confirmation of whether the scan is finished or the number of the scans finished with changing the form of the switches of the scan items displayed on the TCS 60. Therefore, the operator can operate the series of scans without fail in recognizing which scans are finished.

Numerous modifications and variations of the present invention are possible in light of the above technique. It is therefore to be understood that within the scope of the appended claims, the invention may be practiced otherwise than as specifically described herein.

What is claimed is:

1. A medical diagnostic apparatus for collecting data of a plurality of data collection scanning items of a subject, comprising:

an interface for displaying item operator selection elements by which a respective of the items is selected;

a data collecting unit configured to collect data of an object corresponding to the items selected with the item operator selection elements of the interface; and a controller, connected to the interface and the data collecting unit, and configured to control display of the operator selection elements to be in a first form prior to completion of data collection with respect to a data collection operation associated with the respective operator selection element and in a second form different from the first form when the data collection operation associated with the respective operator selection element is completed.

2. The medical diagnostic apparatus according to claim 1, further comprising:

said interface configured to display at least one category element corresponding to plural operator selection elements; and said controller configured to change display of the category element from a first form to a second form upon completion of data collection of all data collection operations associated with operation selection elements corresponding to said at least one category element.

3. The medical diagnostic apparatus according to claim 1, wherein the controller is configured to control display of the second form and display of the number of repetitions completed in regard to a data collection item.

4. The medical diagnostic apparatus according to claim 3, wherein the interface is configured to display the number numerically.

5. The medical diagnostic apparatus according to claim 3, wherein the interface is configured to display the number non-numerically.

6. The medical diagnostic apparatus according to claim 1, wherein the controller is configured to control display of the second form to be different from the first form in at least one of a shape, color and size.

7. The medical diagnostic apparatus according to claim 1, wherein the controller is configured to control display of all of the items to be in the first form according to a command input by the operator.

8. The medical diagnostic apparatus according to claim 1, wherein the interface comprises a touch command screen.

9. The medical diagnostic apparatus according to claim 1, wherein the interface comprises a CRT monitor.

10. The medical diagnostic apparatus according to claim 9, wherein the interface is configured to display the operator selection elements as icons displayed on the CRT monitor.

11. The medical diagnostic apparatus according to claim 1, further comprising:

an input device configured to input information of the subject; and the controller configured to activate only data collection operations corresponding to information input by the input device.

12. The ultrasonic diagnostic apparatus according to claim 11, wherein the controller is configured to control display of the second form to be different from the first form in at least one of a shape, color and size.

13. An ultrasonic diagnostic apparatus capable of performing plural!data collection operations based on an ultrasonic image, comprising:

an interface including a display configured to display operator selection elements each representing a respective data collection item by which an operator can select a respective data collection operation;

a data collection unit configured to collect data corresponding to the item selected with the operator selection elements of the interface;

a controller coupled to the interface and the data collection unit and configured to control the interface to display the operator selection elements so as to change the display from a first form to a second form different from the first form when the selected data collection operation is completed; and a monitor, provided separately from the interface, configured to display at least one of the ultrasonic image and the collected data.

14. The ultrasonic diagnostic apparatus according to claim 13, further comprising:

said interface configured to display at least one category element corresponding to plural operator selection elements; and said controller configured to change display of the category element from a first form to a second form upon completion of data collection of all data collection operations associated with operation selection elements corresponding to said at least one category element.

15. The ultrasonic diagnostic apparatus according to claim 13, wherein the controller is configured to control display of the second form and display of the number of repetitions completed in regard to a data collection item.

16. The ultrasonic diagnostic apparatus according to claim 15, wherein the interface is configured to display the number numerically.

17. The ultrasonic diagnostic apparatus according to claim 15, wherein the interface is configured to display the number non-numerically.

18. The ultrasonic diagnostic apparatus according to claim 13, wherein the controller is configured to control display of all of the items to be in the first form according to a command input by the operator.

19. The ultrasonic diagnostic apparatus according to claim 13, wherein the interface comprises a touch command screen.

20. The medical diagnostic apparatus according to claim 13, wherein the interface comprises a CRT monitor.

21. The medical diagnostic apparatus according to claim 20, wherein the interface is configured to display the operator selection elements as icons displayed on the CRT monitor.

22. The medical diagnostic apparatus according to claim 13, further comprising:

an input device configured to input information of the subject; and the controller configured to activate only data collection operations corresponding to information input by the input device.

23. A medical diagnostic method for collecting data of a plurality of items of an object, comprising:

displaying on an interface of a medical diagnostic apparatus, operation selection elements, each corresponding to one of the items, with which an operator can select at least one of the items, the operation selection elements being displayed in a first predetermined form;

collecting the data of the object corresponding to the selected item selected with the operation selection; and displaying the operation selection element corresponding to a selected item in a second predetermined form different from the first form when the data collection for the selected item finishes.

24. The method of claim 23, comprising:

displaying at least one category element corresponding to plural operator selection elements; and changing display of the category element from a first form to a second form upon completion of data collection of all data collection operations associated with operation selection elements corresponding to said at least one category element.

25. The method of claim 23, comprising:

displaying a number of repetitions completed in regard to a data collection item.

26. The method of claim 25, comprising:

displaying the number numerically.

27. The method of claim 25, comprising:

displaying the number non-numerically.

28. The method of claim 23, comprising:

displaying the second form to be different from the first form in at least one of a shape, color and size.

29. The method of claim 23, comprising:

displaying all of the items to be in the first form according to a command input.

30. The method of claim 23, comprising: displaying the operator selection elements on a touch command screen.

31. The method of claim 23, comprising:

displaying the operator selection elements on a CRT monitor.

32. The method of claim 31, comprising:

displaying the operator selection elements as icons displayed on the CRT monitor.

33. The method of claim 23, further comprising:

inputting information of the subject using an input device; and activating only data collection operations corresponding to information input by the input device.

* * * * *